United States Patent
Hiraoka et al.

(10) Patent No.: US 10,435,553 B2
(45) Date of Patent: Oct. 8, 2019

(54) RESIN COMPOSITION, MOLDED ARTICLE AND FILM INCLUDING VINYLIDENE FLUORIDE-BASED RESIN

(71) Applicant: Mitsubishi Chemical Corporation, Tokyo (JP)

(72) Inventors: Tatsuhiro Hiraoka, Tokyo (JP); Masashi Ikawa, Tokyo (JP); Eiko Okamoto, Tokyo (JP); Hiroshi Hosokawa, Tokyo (JP); Kikue Irie, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 15/917,025

(22) Filed: Mar. 9, 2018

(65) Prior Publication Data
US 2018/0208758 A1 Jul. 26, 2018

Related U.S. Application Data

(63) Continuation of application No. PCT/JP2016/076410, filed on Sep. 8, 2016.

(30) Foreign Application Priority Data

| Sep. 11, 2015 | (JP) | 2015-178994 |
| Sep. 14, 2015 | (JP) | 2015-180411 |
| Sep. 16, 2015 | (JP) | 2015-182383 |
| Sep. 30, 2015 | (JP) | 2015-192417 |

(51) Int. Cl.
| *C08L 27/16* | (2006.01) |
| *C08F 299/00* | (2006.01) |
| *G01N 25/48* | (2006.01) |
| *C08L 33/10* | (2006.01) |
| *C08L 33/08* | (2006.01) |
| *C08L 33/16* | (2006.01) |

(52) U.S. Cl.
CPC ............ *C08L 27/16* (2013.01); *C08F 299/00* (2013.01); *G01N 25/4866* (2013.01); *C08L 33/08* (2013.01); *C08L 33/10* (2013.01); *C08L 33/16* (2013.01); *C08L 2203/16* (2013.01)

(58) Field of Classification Search
CPC ...... C08L 55/005; C08L 101/00; C08L 27/16; C08L 53/00
See application file for complete search history.

(56) References Cited

U.S. PATENT DOCUMENTS

| 7,144,952 | B1 * | 12/2006 | Court et al. | .......... C08F 297/02 525/94 |
| 2011/0207841 | A1 * | 8/2011 | Kosar et al. | .......... B01D 71/34 521/134 |
| 2014/0342224 | A1 * | 11/2014 | Cojocaru et al. | ....... H01M 4/36 429/217 |

FOREIGN PATENT DOCUMENTS

| CN | 102196849 A | 9/2011 |
| CN | 102892816 A | 1/2013 |
| JP | S63-023949 A | 2/1988 |
| JP | S63-308055 A | 12/1988 |
| JP | S63-308056 A | 12/1988 |
| JP | H03-007784 A | 1/1991 |
| JP | 2001-525474 A | 12/2001 |
| WO | 99/29772 A2 | 6/1999 |
| WO | 2011/142453 A1 | 11/2011 |

OTHER PUBLICATIONS

International Search Report issued in related International Patent Application No. PCT/JP2016/076410 dated Nov. 8, 2016.
Chinese Office Action issued in Chinese Application No. 201680052079.X dated Jul. 19, 2019.

* cited by examiner

*Primary Examiner* — Nathan M Nutter
(74) *Attorney, Agent, or Firm* — Morgan, Lewis & Bockius LLP

(57) ABSTRACT

The present invention provides a resin composition including a vinylidene fluoride-based resin (A), having a crystal melting enthalpy of 10 to 45 J/g as measured with a differential scanning calorimeter, and having (2) $I_{Hv}$ of 60 or less as obtained by (1) a light scattering measurement.

14 Claims, No Drawings

RESIN COMPOSITION, MOLDED ARTICLE AND FILM INCLUDING VINYLIDENE FLUORIDE-BASED RESIN

TECHNICAL FIELD

The present invention relates to a resin composition, a molded article and a film that include a vinylidene fluoride-based resin.

BACKGROUND ART

A fluororesin has excellent characteristics such as weather resistance, fire retardancy, heat resistance, antifouling properties, smoothness and chemical resistance, and is suitable as a material of articles exposed to an outdoor environment. Among the fluororesins, vinylidene fluoride-based resins, in particular, polyvinylidene fluoride (hereinafter referred to as "PVDF") has a large difference between a melting point and a decomposition temperature, and is a thermoplastic resin suitable for fabrication. However, the crystal of the PVDF tends to grow up to a size larger than wavelengths of visible light and scatters a part of the visible light, and accordingly the transparency becomes low. Because of this, it has been difficult to apply the PVDF to transparent materials.

Cases of the development of resin materials incorporating the properties of the PVDF have been reported in the past. For example, in Patent Literature 1, a block polymer formed of a block chain compatible with a vinylidene fluoride-based resin and a soft block chain is mixed with a vinylidene fluoride-based resin to reform the flexibility and impact strength of the vinylidene fluoride-based resin. In addition, in Patent Literature 2, an ABC triblock polymer is used to achieve both a thermal deformation temperature and impact performance of the crystalline resin. In any of the literatures, an acrylic-based resin (PMMA) is used as a compatible block with the vinylidene fluoride-based resin.

However, as for the mixture with these block polymers, there are many cases in which mechanical properties and thermal properties of the vinylidene fluoride-based resin are improved by the introduction of domains having different chemical properties, and there is no known example in which both of the transparency and the crystallinity are achieved by controlling the crystal size.

Example 1 of Patent Literature 2 discloses that the appearance becomes transparent by the mixture of the block polymer and the vinylidene fluoride-based resin. However, the specific transmittance is not referred to, and from the result of form observation by a transmission electron microscope, it is merely stated that the matrix is a PVDF+PMMA block mixture. In other words, the increase in the transparency in Example 1 of Patent Literature 2 is not caused by the refinement of the crystal size, but is caused by the decrease in the crystallinity itself.

CITATION LIST

Patent Literature

Patent Literature 1: JP63-308055A
Patent Literature 2: JP2001-525474A

SUMMARY OF INVENTION

Technical Problem

An object of the present invention is to provide a resin composition having many fine crystals by refining a crystal size of a crystalline resin in the resin composition in order to suppress light scattering, while keeping a high degree of crystallinity. Another object of the present invention is to provide a molded article and a film that suppress light scattering by using the resin composition and have high crystallinity and high transparency.

Solution to Problem

Specifically, the present invention has the following features.

[1] A resin composition including a vinylidene fluoride-based resin (A), having a crystal melting enthalpy of 10 to 45 J/g as measured with a differential scanning calorimeter, and having (2) $I_{Hv}$ of 60 or less as obtained by the following (1) light scattering measurement, wherein (1) the light scattering measurement is a measurement in which a molded article of the resin composition sandwiched between two polarizing plates is irradiated with laser light from a normal direction, the transmitted scattered light is projected onto a screen, and the scattered light is detected with a detector, and (2) the $I_{Hv}$ is a value obtained by converting a difference between a light quantity on the screen when directions of polarization of the two polarizing plates are orthogonal to each other in the (1) light scattering measurement and a light quantity on the screen when the molded article of the resin composition is not sandwiched, into a value per unit thickness (1 μm) of the molded article of the resin composition.

[2] The resin composition according to [1], wherein the $I_{Hv}$ is 45 or less.

[3] The resin composition according to [1] or [2], further including an acrylic-based resin (B).

[4] The resin composition according to [3], wherein the acrylic-based resin (B) contains a macromonomer unit.

[5] The resin composition according to [3] or [4], including 20 to 60% by mass of the vinylidene fluoride-based resin (A) and 40 to 80% by mass of the acrylic-based resin (B).

[6] The resin composition according to any one of [3] to [5], wherein the acrylic-based resin (B) is a copolymer satisfying the following (3) and (4):

(3) the acrylic-based resin (B) has a domain (C) compatible with the vinylidene fluoride-based resin (A), and a domain (D) different from the domain (C), and (4) a difference in a solubility parameter between the domain (C) and the domain (D) is 0.010 to 0.270.

[7] The resin composition according to [6], wherein the domain (D) contains 30 to 70% by mass of a monomer unit of which a mass ratio is the largest among monomer units constituting the domain (C).

[8] The resin composition according to [6] or [7], wherein a mass average molecular weight of the polymer or polymer chain constituting the domain (C) is 5,000 to 45,000.

[9] The resin composition according to any one of [3] to [8], including 0.01 to 3.0 parts by mass of polytetrafluoroethylene per 100 parts by mass in total of the vinylidene fluoride-based resin (A) and the acrylic-based resin (B).

[10] The resin composition according to any one of [3] to [9], including acrylic-modified polytetrafluoroethylene so that a content of polytetrafluoroethylene is 0.01 to 3.0 parts by mass per 100 parts by mass in total of the vinylidene fluoride-based resin (A) and the acrylic-based resin (B).

[11] A molded article obtained by molding the resin composition according to any one of [1] to [10].

[12] A film obtained by molding the resin composition according to any one of [1] to [10].

[13] The film according to [12], having a thickness of 350 μm or less.

[14] The film according to [12], having the arithmetic mean roughness of a surface of 50 nm or less.

Advantageous Effects of Invention

The resin composition of the present invention suppresses light scattering by controlling the crystal size and has both of high crystallinity and high transparency. In addition, the molded article of the present invention suppresses the light scattering by using the resin composition of which the crystal size is controlled and has the high crystallinity and the high transparency. Furthermore, the film of the present invention suppresses the light scattering by using the resin composition of which the crystal size is suppressed and has the high crystallinity and the high transparency.

DESCRIPTION OF EMBODIMENTS

The resin composition according to the present invention is a resin composition including a vinylidene fluoride-based resin (A), having a crystal melting enthalpy of 10 to 45 J/g as measured with a differential scanning calorimeter, and having (2) $I_{Hv}$ of 60 or less as obtained by the following (1) light scattering measurement, wherein (1) the light scattering measurement is a measurement in which a molded article of the resin composition sandwiched between two polarizing plates is irradiated with laser light from a normal direction, the transmitted scattered light is projected onto a screen, and the scattered light is detected with a detector, and (2) the $I_{Hv}$ is a value obtained by converting a difference between a light quantity on the screen when directions of polarization of the two polarizing plates are orthogonal to each other in the (1) light scattering measurement and a light quantity on the screen when the molded article of the resin composition is not sandwiched, into a value per unit thickness (1 μm) of the molded article of the resin composition.

Each component constituting the resin composition according to the present invention will be described below.

<Vinylidene Fluoride-based Resin (A)>

Examples of the vinylidene fluoride-based resin (A) include a copolymer containing 70% by mass or more of a vinylidene fluoride unit, or a homopolymer of vinylidene fluoride (PVDF). In the vinylidene fluoride-based resin (A), the higher the content of the vinylidene fluoride unit is, the better the crystallinity becomes, and accordingly the higher content is preferable. Hereinafter, the "vinylidene fluoride-based resin (A)" is also referred to simply as "resin (A)".

When the resin (A) is the above described copolymer, examples of the monomer copolymerized with vinylidene fluoride include hexafluoropropylene and tetrafluoroethylene.

Examples of a method of polymerizing the resin (A) include known polymerization methods such as suspension polymerization and emulsion polymerization methods. The degree of crystallinity and mechanical properties of the obtained resin (A) vary depending on the polymerization method.

PVDF is preferable as the resin (A) because of having a large difference between the melting point and the decomposition temperature and being suitable for fabrication.

In addition, resins having a high crystalline melting point are preferable as the resin (A). In addition, in the present invention, the crystalline melting point means a peak melting temperature of crystal at the time when the crystalline melting point is measured according to JIS K7121, 3. (2). The crystalline melting point of the resin (A) is preferably 150° C. or higher, and more preferably is 160° C. or higher, from the viewpoint of the thermal stability of the resin composition. In addition, the upper limit of the crystalline melting point is preferably 170° C., which is equal to the crystalline melting point of the PVDF. Specifically, the crystalline melting point of the resin (A) is preferably 150° C. or higher and 170° C. or lower, and more preferably 160° C. or higher and 170° C. or lower.

The mass average molecular weight (Mw) of the resin (A) is preferably 100,000 to 1,000,000, more preferably 150,000 to 800,000, and further preferably 180,000 to 700,000, in order to obtain a melt viscosity suitable for fabrication. Here, the mass average molecular weight can be measured using gel permeation chromatography (GPC). Specifically, for example, a solvent such as tetrahydrofuran or water can be used as an eluent, and can be determined as the molecular weight in terms of polymethyl methacrylate.

Examples of commercially available products (all of which are brand names) of the resin (A) include: Kynar (registered trademark) 720, Kynar 710, Kynar 740 and Kynar 760 manufactured by Arkema Co.; KF#850 manufactured by Kureha Corporation; and Solef (registered trademark) 1006, Solef 1008, Solef 1015, Solef 6010, Solef 6012 and Solef 6008 manufactured by Solvay Specialty Polymers Co.

The resins (A) may be used solely, or in combination of two or more thereof.

<Acrylic-based Resin (B)>

Examples of components other than the resin (A), which are included in the resin composition of the present invention, include polymers that contain methyl (meth)acrylate, ethyl (meth)acrylate, vinyl acetate and vinyl methyl ketone as monomer units. Among these polymers, the polymers which contain (meth)acrylates as the monomer unit (hereinafter referred to as "acrylic-based resin (B)" or also simply referred to as "resin (B)") are preferable from the viewpoint of compatibility with the resin (A).

The resin (B) is a polymer that contains a (meth)acrylate as a monomer unit. From the viewpoint of having good compatibility with the resin (A), the resin (B) is preferably a polymer containing a methyl methacrylate unit.

Moreover, the "(meth)acrylate" used herein means "acrylate" or "methacrylate".

Examples of the monomer units other than methyl methacrylate, which may be contained in the resin (B), include: monomer units derived from alkyl (meth)acrylates such as methyl acrylate, ethyl (meth)acrylate, n-propyl (meth)acrylate, isopropyl (meth)acrylate, n-butyl (meth)acrylate, isobutyl (meth)acrylate, t-butyl (meth)acrylate, n-pentyl (meth)acrylate, n-hexyl (meth)acrylate, cyclohexyl (meth)acrylate, n-octyl (meth)acrylate, 2-ethylhexyl (meth)acrylate, dodecyl (meth)acrylate, stearyl (meth)acrylate, isobornyl (meth)acrylate, 2-hydroxyethyl (meth)acrylate and benzyl (meth)acrylate; monomer units derived from aromatic vinyl monomers such as styrene, α-methylstyrene, p-methylstyrene, o-methylstyrene and t-butylstyrene; monomer units derived from vinyl cyanide monomers such as acrylonitrile and methacrylonitrile; monomer units derived from glycidyl group-containing monomers such as glycidyl (meth)acrylate; monomer units derived from vinyl carboxylate monomers such as vinyl acetate and vinyl butyrate; monomer units derived from olefin monomers such as ethylene, propylene and isobutylene; monomer units derived from diene-based monomers such as butadiene and isoprene;

and monomer units derived from unsaturated carboxylic acid monomers such as maleic acid and maleic anhydride.

Among these other monomer units, the alkyl (meth) acrylate units are preferable from the viewpoint of polymerizability and compatibility with methyl methacrylate; and the methyl acrylate unit, the ethyl (meth)acrylate unit, the n-propyl (meth)acrylate unit, the isopropyl (meth)acrylate unit and the n-butyl (meth)acrylate unit are more preferable, from the viewpoint of the glass transition temperature (Tg) of the polymer.

The resin (B) may contain one of the other monomer units or may contain two or more thereof.

The resin (B) is preferably one which causes microphase separation when molded alone. If the resin (B) has a microphase-separated structure, crystallization of the resin (A) proceeds in the vicinity of the microphase-separated structure when mixed with the resin (A).

Furthermore, the resin (B) preferably has a domain (C) compatible with the resin (A) (hereinafter also referred to as "domain (C)"), and a domain (D) different from the domain (C). In addition, the resin (B) is more preferably formed of the domain (C) and the domain (D) different from the domain (C). In this case, when the resin (B) and the resin (A) have been mixed, the resin (A) becomes compatible with the domain (C), and the crystallization proceeds in the vicinity of the domain (C) when the mixture has been cooled.

Moreover, in the present invention, the "compatibility" used herein means that a single Tg which is not derived from any of dissimilar polymers is observed in a molded article prepared by mixing the dissimilar polymers. In addition, the dissimilar polymers mean polymers having different compositions from each other.

In the present invention, the "domain" means one phase constituting the phase-separated structure. When the molded article prepared by mixing dissimilar polymers has the phase-separated structure, Tg derived from each domain is observed.

In the present invention, the "different domain" means a domain in which the content of at least one monomer among the monomers constituting the domain is different by 5% or more by mass ratio. The above described content is preferably different by 10% or more.

However, it may be occasionally difficult to determine compatibility/incompatibility only by the number of Tg. For example, when the Tg after the domain (C) and the resin (A) have mutually dissolved and the Tg of the domain (D) are the same temperature by chance, the mixed molded article appears to have the single Tg. Because of this, it is necessary to check the compatibility/incompatibility by changing a mixing ratio, or by other methods.

The smaller the domain size is, the more preferable the phase-separated structure of the resin (B) is. When the domain size is small, the refinement of the crystals in the resin (A) tends to easily occur, and high crystallinity and high transparency can be easily achieved at the same time. Furthermore, the lowering in the optical performance due to the difference in the refractive index between domains of phases becomes unlikely to occur.

The size of each domain is preferably 500 nm or less, more preferably 300 nm or less, and further preferably 100 nm or less. When the domain size is 500 nm or less, the wavelength in the visible light region is unlikely to be scattered, and the high transparency is obtained. The lower limit of the size of each domain is approximately 20 nm. Specifically, the size of each domain is preferably 20 to 500 nm, more preferably 20 to 300 nm, and further preferably 20 to 100 nm.

Moreover, the size of the domain means the length in the long axis direction of the island phase in the case of the sea-island structure, and means the shortest distance between the interface between the domains and the nearest interface thereof, in the case of a bicontinuous structure. The size of the domain means an average value obtained by preparing an observation piece having a thickness of 20 to 200 nm from the molded article, observing the observation piece with a transmission electron microscope, and measuring 5 pieces of arbitrary domains.

The phase-separated structure of the single resin (B) may be the sea-island structure or the bicontinuous structure. The physical properties of the molded article depend on the phase-separated structure after mixing the resin (B) with the resin (A).

As for the mass average molecular weight (Mw) of the resin (B), the mass average molecular weight is preferably high in order to keep the mechanical strength when the resin composition has been formed into the molded article, but if the mass average molecular weight is too high, the fluidity decreases, which causes the lowering of the moldability. The mass average molecular weight of the resin (B) is preferably 40,000 to 1,000,000, more preferably 50,000 to 750,000, and further preferably 60,000 to 500,000, from the viewpoint of achieving both of the mechanical strength and the moldability.

The molecular weight distribution (PDI) of the resin (B) is preferably 1.8 to 10.0. If the PDI is 1.8 or more, the resin (B) contains a low molecular weight substance, and accordingly tends to easily secure fluidity suitable for molding. In addition, if the PDI is 10.0 or less, the quality of the molded article easily becomes stable. From the viewpoint of compatibility between the mass average molecular weight and the fluidity, PDI is more preferably 1.8 to 9.0, and further preferably 2.0 to 8.0.

[Domain (C)]

The domain (C) is a domain compatible with the vinylidene fluoride-based resin (A).

Examples of polymers or polymer chains constituting the domain (C) (hereinafter referred to as "polymer constituting the domain (C)") include those containing 51% by mass or more of a segment compatible with the resin (A). In order to secure the compatibility with the resin (A), the content of the segment compatible with the resin (A) is preferably 60% by mass or more, more preferably 80% by mass or more, and further preferably 90% by mass or more.

Examples of the above described segments include monomer units derived from monomers such as methyl (meth) acrylate, ethyl (meth)acrylate, vinyl acetate and vinyl methyl ketone. The polymer constituting the domain (C) may contain one of the above segments solely or may contain two or more thereof.

The molecular weight of the polymer constituting the domain (C) is preferably small, from the viewpoint of promoting the crystallization of the resin (A) when the resin (A) and the resin (B) have been mixed. The mass average molecular weight (Mw) of the polymer constituting the domain (C) is preferably 5,000 to 45,000. If the mass average molecular weight of the polymer constituting the domain (C) is 5,000 or more, the domain (C) and the domain (D) lower the compatibility, and become likely to cause the phase separation. In addition, if the above described mass average molecular weight is 45,000 or less, the entanglement between the domain (C) and the resin (A) becomes small, which does not inhibit the crystallization of the resin (A).

From the viewpoint of forming the phase-separated structure, the above described mass average molecular weight is more preferably 40,000 or less, and further preferably 36,000 or less. In addition, the above described mass average molecular weight is more preferably 10,000 or more, and further preferably 15,000 or more. Specifically, the above described mass average molecular weight is more preferably 10,000 or more and 40,000 or less, and further preferably 15,000 or more and 36,000 or less.

As for a method of introducing the domain (C) into the resin (B), known methods such as a method of forming a block chain of a block copolymer or a graft copolymer, and a method of mixing the domain (C) with a mixture thereof can be used. Furthermore, as for a method of synthesizing the above described block chain of the block copolymer or the graft copolymer, there are living radical polymerization such as ATRP (Atom Transfer Radical Polymerization), anion polymerization, and polymerization using a macromonomer. Among these, the polymerization using the macromonomer is preferable from the viewpoint of productivity such as a polymerization speed and the number of processes. Moreover, in the present invention, the macromonomer means a high-molecular compound having a polymerizable functional group.

The domain (C) preferably contains a macromonomer unit in that the domain (C) can easily be introduced into the resin (B) by copolymerization, and can simply adjust the domain size and the phase-separated structure to be formed with the domain (D). Specifically, the resin (B) preferably contains the macromonomer unit. The content of the macromonomer unit in the domain (C) is preferably 80% by mass or more, and more preferably 90% by mass or more. In addition, the content of the macromonomer unit in the resin (B) is preferably 20 to 60% by mass, and more preferably 30 to 50% by mass.

For the macromonomer, a commercially available product may be employed, or the macromonomer may be produced from a monomer by a known method. Examples of methods of producing the macromonomer include a method of producing the macromonomer using a cobalt chain transfer agent, a method involving using an α-substituted unsaturated compound such as α-bromomethylstyrene as a chain transfer agent, a method involving chemically bonding a polymerizable group, and a method involving thermal decomposition.

The macromonomer unit contained in the domain (C) (macromonomer unit contained in the resin (B)) preferably contains a methyl methacrylate unit, from the viewpoint of compatibility with the resin (A). The content of the methyl methacrylate unit in the macromonomer unit contained in the domain (C) is preferably 50% by mass or more, more preferably 70% by mass or more, and further preferably 80% by mass or more.

[Domain (D)]

The domain (D) is a domain different from the above described domain (C). The domain (D) preferably contains 30 to 70% by mass of a monomer unit having the largest mass ratio among the monomer units constituting the above described domain (C), from the viewpoint of compatibility with the resin (A). The above described monomer unit contained in the domain (D) is more preferably 35 to 65% by mass.

Examples of the monomer units other than the above described monomer unit constituting the domain (D) include: monomer units derived from alkyl (meth)acrylates such as n-propyl (meth)acrylate, isopropyl (meth)acrylate, n-butyl (meth)acrylate, isobutyl (meth)acrylate, t-butyl (meth)acrylate, n-pentyl (meth)acrylate, n-hexyl (meth)acrylate, cyclohexyl (meth)acrylate, n-octyl (meth)acrylate, 2-ethylhexyl (meth)acrylate, dodecyl (meth)acrylate, stearyl (meth)acrylate, isobornyl (meth)acrylate, 2-hydroxyethyl (meth)acrylate and benzyl (meth)acrylate; monomer units derived from aromatic vinyl monomers such as styrene, α-methylstyrene, p-methylstyrene, o-methylstyrene and t-butylstyrene; monomer units derived from vinyl cyanide monomers such as acrylonitrile and methacrylonitrile; monomer units derived from glycidyl group-containing monomers such as glycidyl (meth)acrylate; monomer units derived from vinyl carboxylate monomers such as vinyl acetate and vinyl butyrate; monomer units derived from olefin monomers such as ethylene, propylene and isobutylene; monomer units derived from diene-based monomers such as butadiene and isoprene; and monomer units derived from unsaturated carboxylic acid monomers such as maleic acid and maleic anhydride. The polymer constituting the domain (D) may contain one of the above described monomer units or may contain two or more thereof.

Among these other monomer units, the alkyl (meth) acrylates are preferable, from the viewpoint of the polymerizability and compatibility with the methyl methacrylate, and the ethyl (meth)acrylate, the n-propyl (meth)acrylate, the isopropyl (meth)acrylate and the n-butyl (meth) acrylate are more preferable, from the viewpoint of Tg of the polymer.

(Sp Value)

The domain (D) has a difference in a solubility parameter (SP) with the domain (C) of preferably 0.010 to 0.270, more preferably 0.080 to 0.250, and further preferably 0.100 to 0.200, from the viewpoint of the size of the microphase-separated structure.

Moreover, in the present invention, the solubility parameter (SP) means a value estimated according to the Fedors method. The solubility parameter represents a measure of the affinity between substances, and substances having a small difference in the solubility parameter have such properties as to be easily mixed with each other. The value of the solubility parameter can be calculated according to the following expression (1):

$$SP=(\Delta H/V)^{1/2} \qquad (1).$$

Moreover, in the expression (1), $\Delta H$ represents a molar heat of vaporization (J/mol), and V represents a molar volume (cm$^3$/mol). In addition, as the $\Delta H$ and V, the sum ($\Delta H$) of the molar heats of vaporization ($\Delta$ei) and the sum (V) of the molar volumes ($\Delta$vi) of the atomic groups were used, which are described in "POLYMER ENGINEERING AND SCIENCE, February, 1974, Vol. 14, No. 2, Robert F. Fedors (pages 147 to 154).

Moreover, the solubility parameter of the copolymer was calculated in consideration of the molar ratio of the monomer composition of the copolymer.

<Additive>

The resin composition of the present invention may include an additive as needed, in a range that does not impair the optical performance and the mechanical characteristics. The amount of the additive is preferably as small as possible; and is preferably 20 parts by mass or less, more preferably 10 parts by mass or less, and further preferably 5 parts by mass or less, per 100 parts by mass of the resin composition. Examples of the additives include ultraviolet absorbers, light stabilizers, heat-resistant stabilizers, antiblocking agents such as synthetic silica and silicone resin powder, plasticizers, antibacterial agents, fungicides, bluing agents and antistatic agents.

Examples of the ultraviolet absorbers include: benzoate-based compounds, benzophenone-based compounds, benzotriazole-based compounds, triazine-based compounds, salicylate-based compounds, acrylonitrile-based compounds, metal complex salt-based compounds and hindered amine-based compounds; and inorganic particles such as ultrafine titanium oxide having a particle diameter of approximately 0.01 to 0.06 μm and ultrafine zinc oxide having a particle diameter of approximately 0.01 to 0.04 μm. These ultraviolet absorbers may be used solely, or in combination of two or more thereof.

Examples of the light stabilizers include hindered amine-based or phenol-based light stabilizers such as a N—H type, a N—CH$_3$ type, a N-acyl type and a N—OR type.

As ultraviolet absorbers or antioxidants, for example, a polymer type in which the above described ultraviolet absorber or antioxidant is chemically bonded to a main chain or a side chain constituting the polymer may be used.

<Resin Composition>

The resin composition of the present invention is a resin composition including the resin (A), having a crystal melting enthalpy of 10 to 45 J/g as measured with a differential scanning calorimeter, and having (2) $I_{Hv}$ of 60 or less as obtained by the above described (1) light scattering measurement.

The resin composition of the present invention preferably further includes the above described acrylic-based resin (B). In the case where the resin composition includes the resin (B), as for the content of each of the resin (A) and the resin (B) in the resin composition, the content of the resin (A) is preferably 20 to 60% by mass, and the content of the resin (B) is preferably 40 to 80% by mass. Here, the total content of the resin (A) and the resin (B) is to be 100% by mass. Specifically, the resin composition of the present invention is preferably a resin composition formed of 20 to 60% by mass of the vinylidene fluoride-based resin (A) and 40 to 80% by mass of the above described acrylic-based resin (B).

When the content of the resin (A) in the resin composition is 20% by mass or more, the resin (A) tends to be easily crystallized. In addition, when the content of the resin (A) is 60% by mass or less, the molded article prepared by using the resin composition has a higher transparency. In addition, the content of the resin (A) in the resin composition is more preferably 30 to 60% by mass, and further preferably 35 to 55% by mass, from the viewpoint of use in the production of the molded article having both high crystallinity and high transparency.

When the content of the resin (B) in the resin composition is 40 to 80% by mass, it becomes easy to suppress the crystal size while keeping the crystallinity of the resin (A). The content of the resin (B) is more preferably 40 to 70% by mass, and further preferably 45 to 65% by mass.

In the resin composition of the present invention, crystals are refined irrespective of the molding method, and accordingly the transparency of the obtained molded article can be easily obtained. The higher the transparency of the molded article is, the more application range to transparent materials such as thick films and sheets expands.

Moreover, the high transparency means that in the case of the molded article having a thickness of 200 μm, for example, the total light transmittance measured according to JIS K7361-1 is 88 to 100%. The higher the total light transmittance is, the more preferred the molded article is. Specifically, the total light transmittance is preferably 90% or more, and more preferably 92% or more.

In addition, in the case of the molded article having the thickness of 200 μm, a haze (HZ) measured according to JIS K7136 is preferably 0 to 10%, more preferably 0 to 7%, and further preferably 0 to 5%.

(Crystal Melting Enthalpy)

In order to incorporate the crystallinity of the resin (A), the resin composition of the present invention has a crystal melting enthalpy in the range of 10 to 45 J/g as measured with a differential scanning calorimeter.

The crystal melting enthalpy depends on the content of the resin (A) in the resin composition. Accordingly, when the content of the resin (B) is increased so that the effect of suppressing the crystal size is obtained, the value decreases. From the viewpoint of achieving both of the amount of crystals and the suppression of crystal size, the crystal melting enthalpy is preferably 10 to 35 J/g, and more preferably 10 to 30 J/g. Moreover, in the present invention, the crystal melting enthalpy means a crystal melting enthalpy measured according to JIS K7121, 3. (2).

(Light Scattering Measurement)

In the present invention, the light scattering measurement is a measurement in which a molded article of the resin composition sandwiched between two polarizing plates is irradiated with laser light from a normal direction, the transmitted scattered light is projected onto a screen, and the scattered light is detected with a detector. By this measurement, $I_{Hv}$ which will be described later can be determined, and the scattered light intensity in the molded article can be estimated.

In the measurement, a general laser such as a YAG laser and a He—Ne laser can be used. In points of the safety and the cost, the He—Ne laser is preferable.

Laser light having a wavelength in the visible light region is preferable, because of being visible on the screen. Specifically, laser light of 400 to 760 nm is preferable, and laser light of 460 to 700 nm is more preferable.

The output of the laser is preferably 1 mW or more, more preferably 3 mW or more, and further preferably 5 mW or more, in order to detect the scattered light.

As for the polarizing plate to be used in the measurement, a polarizing plate made of a general material such as glass or a resin can be used. In addition, a general polarizing plate such as a polarizing film type, a crystal type and a wire grid type can be used. The higher the contrast is, the more preferable the polarizing plate is, because the transmitted light at the time when the polarizing plate is orthogonal decreases. Specifically, the contrast is preferably 100 or more, more preferably 1,000 or more, and further preferably 5,000 or more.

The molded article of the resin composition to be used in the measurement preferably has an incidence plane and an exit plane which are parallel to each other and are smooth, from the viewpoint of preventing the reflection and refraction of the laser light. Examples of the molded article include an injection molded article, a sheet, and a film. The sheet or the film is preferable, and the film is most preferable, in that the molded article which is smooth and has a small thickness is obtainable.

Examples of a method for obtaining a molded article of a resin composition to be used in the measurement include injection molding, calendering, blow molding, extrusion, pressing and thermoforming. The injection molding, the extrusion and the pressing are preferable in that a smooth molded article is obtainable.

In addition, the thickness of the molded article is preferably as thin as possible, in that the multiple scattering is prevented which occurs when the laser light passes through the molded article. Specifically, the thickness of the molded article is preferably 3 mm or less, more preferably 1 mm or less, and further preferably 0.5 mm or less.

As for the detector to be used in the measurement, a CCD camera, a photomultiplier or the like can be used. The CCD camera is preferable from the viewpoint of a detection speed and availability.

In order to quantify a value of scattered light intensity, the detector is preferably a detector which can set the gamma value at 1.0. In addition, the detector can preferably set the exposure time so that the detected light amount does not exceed the limit. The exposure time is preferably 200 to 50,000 µs, more preferably 500 to 40,000 µs, and further preferably 1,000 to 30,000 µs. The smaller the sensitivity (gain) is, the more preferable the detector is, because the light quantity can be measured with higher precision. Specifically, the sensitivity is preferably 3 or less, more preferably 1 or less, and further preferably 0.1 or less.

($I_{Hv}$)

The $I_{Hv}$ of the resin composition of the present invention when formed into a molded article is 60 or less, preferably 45 or less, and more preferably 30 or less.

In the present invention, the $I_{Hv}$ is a value obtained by converting a difference between a light quantity on a screen when directions of polarization of two polarizing plates are orthogonal to each other in light scattering measurement and a light quantity on the screen when the molded article of the resin composition is not sandwiched, into a value per unit thickness (1 µm) of the molded article of the resin composition; and is determined by the following expression (2). Here, the directions of the polarization of the two polarizing plates remain orthogonal, even when the molded article is not sandwiched therebetween. The scattering intensity due to the optical anisotropy of the molded article can be estimated from the value of the $I_{Hv}$. The optical anisotropy originates in orderliness of crystals and the like, and accordingly the $I_{Hv}$ is an index which indicates the influence of the crystal size and the amount of crystals.

$$I_{Hv} = (A_{Hv} - A_{Hv0})/d \quad (2)$$

Moreover, in the expression (2), $A_{Hv}$ is a total value of light quantities calculated with the CCD camera in the case where the molded article is sandwiched, $A_{Hv0}$ is a total value of light quantities in the case where the molded article is not sandwiched, and d is a thickness (µm) of the molded article.

The crystallization temperature of the resin composition is preferably 95 to 145° C., more preferably 105 to 140° C., and further preferably 110 to 140° C. When the crystallization temperature is high, the molded article exhibits a sufficient crystallization speed at the time of molding, and accordingly even if the cooling speed is fast, the molded article exhibits a sufficient degree of crystallinity. In addition, when the crystallization temperature is 140° C. or lower, the resin composition becomes unlikely to lose fluidity during being molded, and processing such as stretching becomes easy.

<Resin Composition Including Polytetrafluoroethylene>

The resin composition of the present invention may further include polytetrafluoroethylene (PTFE) in addition to the resin (A), the resin (B) and optional components. The PTFE is obtained by the polymerization of a monomer which contains tetrafluoroethylene as a main component. The tetrafluoroethylene and another monomer may be copolymerized to an extent that does not impair the properties of the PTFE.

Examples of other monomers (copolymerization components) to be copolymerized include fluorine-containing olefins such as hexafluoropropylene, chlorotrifluoroethylene and fluoroalkylethylene; and fluorine-containing alkyl (meth)acrylate such as perfluoroalkyl (meth)acrylate.

The content of the copolymerization component is preferably 10% by mass or less per 100% by mass in total of the tetrafluoroethylene and the copolymerization component.

Preferably, the PTFE is not an aggregate but is particles having an average particle size of 10 µm or less. Because the particle diameter of the PTFE is small and is not aggregated, the PTFE easily becomes uniformly dispersed in the resin composition when being blended therein.

When the resin composition of the present invention includes the polytetrafluoroethylene (PTFE), the resin composition of the present invention preferably includes 0.01 to 3.0 parts by mass of the PTFE per 100 parts by mass in total of the resin (A) and the resin (B).

Hereinafter, the "resin composition including PTFE" is also referred to simply as "PTFE-containing resin composition".

When the PTFE-containing resin composition includes 0.01 parts by mass or more of the PTFE, the PTFE acts as a crystal nucleating agent and increases the crystallization speed. On the other hand, when a shearing force is applied to the PTFE at the time of melt molding, the PTFE is fibrillated by the melt tension to increase the melt viscosity of the PTFE-containing resin composition. However, when the content of the PTFE is 3.0 parts by mass or less, a melt viscosity suitable for fabrication is kept.

From the viewpoint of achieving both of the crystallization speed and the melt viscosity, the content of the PTFE in the PTFE-containing resin composition is more preferably 0.05 to 1.0 parts by mass per 100 parts by mass in total of the resin (A) and the resin (B), further preferably 0.07 to 0.5 parts by mass, and particularly preferably 0.08 to 0.3 parts by mass.

In order to improve the dispersibility in the resin composition, it is preferable to use modified PTFE as the PTFE, and more preferable to use acrylic-modified PTFE, particularly from the viewpoint of not impairing the compatibility with the resin (A).

In the case where the modified PTFE is used, the resin composition may include the modified PTFE so that the PTFE is 0.01 to 3.0 parts by mass per 100 parts by mass in total of the resin (A) and the resin (B), based on the proportion of the PTFE in the modified PTFE.

Examples of the acrylic-modified PTFE include a modified resin obtained by an operation of dispersing PTFE and an acrylic resin in the same dispersion medium, and then drying up the solid matter. By using the acrylic-modified PTFE, the PTFE easily becomes uniformly dispersed in the resin composition.

The Tg of the acrylic-modified PTFE is preferably 40 to 80° C. If the Tg of the acrylic-modified PTFE is 40° C. or higher, the acrylic-modified PTFE resists causing blocking in itself, and is excellent in the handleability of the powder. In addition, if the Tg of the acrylic-modified PTFE is 80° C. or lower, in the case where the acrylic-modified PTFE is obtained by synthesis, the acrylic-modified PTFE is excellent in powder characteristics, for example, when the solid matter is collected, the generation of the fine powder is suppressed. Here, the Tg is measured by differential scanning calorimetry.

In order that the acrylic-modified PTFE exhibits the nucleating agent effect of acting as a primary nucleus of the crystal, the acrylic-modified PTFE preferably contains 10% by mass or more of PTFE, more preferably 30% by mass or more, and further preferably 50% by mass or more in 100% by mass of the acrylic-modified PTFE. In addition, from the viewpoint of securing dispersibility, the acrylic-modified PTFE preferably contains 90% by mass or less of the PTFE in 100% by mass of itself. Specifically, the content of the PTFE in 100% by mass of the acrylic-modified PTFE is preferably 10% by mass or more and 90% by mass or less, more preferably 30% by mass or more and 90% by mass or less, and further preferably 50% by mass or more and 90% by mass or less.

The acrylic-modified portion constituting the acrylic-modified PTFE is preferably, for example, a polymer of a monomer compatible with the resin (A), from the viewpoint of securing the transparency of the molded article.

Examples of the monomers compatible with the resin (A) include methyl (meth)acrylate, ethyl (meth)acrylate and vinyl acetate. These monomers may be used solely, or in combination of two or more thereof. The above described acrylic-modified portion is preferably a polymer of single methyl (meth)acrylate or a copolymer containing 50% by mass or more of methyl (meth)acrylate units, from the viewpoint of ease of emulsion polymerization and compatibility with PVDF.

A mass average molecular weight of the acrylic-modified portion constituting the acrylic-modified PTFE is preferably 20,000 to 100,000, and more preferably 20,000 to 50,000. When the mass average molecular weight of the acrylic-modified portion is 20,000 or more, the mechanical properties of the blended resin composition become unlikely to be impaired. In addition, when the mass average molecular weight of the acrylic-modified portion is 100,000 or less, the fluidity of the blended resin composition at the time of melting becomes unlikely to be impaired.

As for the acrylic-modified PTFE, a synthesized one may be used, or a commercially available product may also be used.

Examples of a method for synthesizing the acrylic-modified PTFE include a latex blending method using an aqueous dispersion liquid of PTFE and an aqueous dispersion liquid of an acrylic resin.

Examples of the aqueous dispersion liquid of PTFE include Fluon (registered trademark) AD-1, Fluon AD-936, Fluon AD-915L, Fluon AD-915E, Fluon AD-939L and Fluon AD-939E (all of which are brand names, manufactured by Asahi Glass Co., Ltd.); Polyflon (registered trademark) D-1 and Polyflon D-2 (all of which are brand names, manufactured by Daikin Industries, Ltd.); and Teflon (registered trademark) 30J (brand name, manufactured by Du Pont-Mitsui Fluorochemicals Company, Ltd.). These aqueous PTFE dispersion liquids may be used solely, or in combination of two or more thereof.

Examples of the commercially available acrylic-modified PTFE include Metablen (registered trademark) A-3000, Metablen A-3700, Metablen A-3750 and Metablen A-3800 (all of which are brand names, manufactured by Mitsubishi Rayon Co., Ltd.).

A crystallization speed of the PTFE-including resin composition of the present invention can be determined from a crystallization temperature observed by differential scanning calorimetry. The meaning holds that the higher the crystallization temperature is, the faster the crystallization speed is.

Moreover, in the present invention, the crystallization temperature means a value of the peak top of the crystallization peak observed in the process of temperature falling at 10° C./min from 200° C.

The crystallization temperature of the PTFE-including resin composition is preferably 110 to 145° C., more preferably 115 to 140° C., and further preferably 120 to 140° C. When the crystallization temperature is 110° C. or higher, the resin composition exhibits a sufficient crystallization speed at the time of melt molding, and accordingly is quickly solidified in a cooling process of thermoforming; and the molded article can easily be taken out. In addition, when the crystallization temperature is 145° C. or lower, the resin composition becomes unlikely to lose fluidity during being molded, and processing such as stretching becomes easy.

The PTFE-including resin composition is excellent in moldability because the crystallization speed increases due to the nucleating agent action of the PTFE. Specifically, a transparent material incorporating the characteristics of the crystalline resin can be easily achieved. Examples of the characteristics of the crystalline resin include heat resistance, chemical resistance and low water absorptivity. In addition, the properties of the resin A which the molded article using the PTFE-including resin composition of the present invention can adopt, also include fire retardancy and weather resistance, in addition to the characteristics of the above described crystalline resin.

Thus, the PTFE-including resin composition of the present invention can simply and comparatively inexpensively provide a molded article having the high crystallinity and high transparency.

The PTFE-including resin composition tends to easily acquire transparency due to an effect of crystal refinement regardless of the molding method. The higher the transparency of the molded article is, the more application range to transparent materials such as thick films and sheets expands.

<Method for Producing Resin Composition>

The resin composition of the present invention can be prepared by blending a predetermined amount of the above described essential components and optional components and kneading the components in a usual kneader such as a roll, a Banbury mixer, a single screw extruder and a twin screw extruder. The resin composition is usually preferably formed into a pellet shape. Thus obtained resin composition of the present invention simply and comparatively inexpensively provides a molded article having the high crystallinity and high transparency in various molding methods.

<Molded Article>

The molded article of the present invention is the one obtained by molding the resin composition of the present invention. Examples of the molding method of the resin composition include injection molding, calendering, blow molding, extrusion, pressing, thermoforming, and melt spinning.

Examples of the molded articles to be obtained by using the resin composition include a film, a sheet, a layered product of a plurality of films or sheets, an injection molded article, a hollow molded article, a pipe, a square bar, a deformed article, a thermoformed article and a fiber. Among these, the film is particularly preferable from the viewpoint of being excellent in the transparency.

<Film>

In general, films having thinner thickness tend to provide higher transparency. Because of this, the thickness of the film of the present invention is preferably 350 µm or less, more preferably 300 µm or less, and further preferably 250 µm or less.

Moreover, in the present invention, the thickness of the film means an average value of measured values obtained by measuring arbitrary three portions in a direction perpendicular to (TD direction) the flow direction at the time of film formation.

When the surface of the film is rough, an external haze is generated due to light scattering on the film surface, and the transparency is lowered. Because of this, the arithmetic mean roughness (Ra) of the film is preferably 50 nm or less, and more preferably 40 nm or less.

<Application of Film>

Examples of applications of the film of the present invention include: applications to automotive exteriors such as a weather strip, a bumper, a bumper guard, a side mud guard, a body panel, a spoiler, a front grill, a strut mount, a wheel cap, a center pillar, a door mirror, a center ornament, a side molding, a door molding, a window molding, a window, a headlamp cover, a tail lamp cover and a windshield component; applications for automotive interiors such as an instrument panel, a console box, a meter cover, a door lock bezel, a steering wheel, a power window switch base, a center cluster and a dashboard; applications to a front panel, a button, an emblem and a surface decorative material of AV equipment, furniture products and the like; applications to a housing, a display window, buttons and the like of a mobile phone; applications to exterior materials for furniture; applications to interior materials for building such as a wall, a ceiling and a floor; applications to exterior materials for buildings such as an outer wall such as a siding, a fence, a roof, a door and a bargeboard; applications to surface cosmetic materials of furniture such as a window frame, a door, a handrail, a threshold and a head jamb; various displays; optical applications such as a Fresnel lens, a polarizing film, a polarizer protective film, a phase difference film, a light diffusion film, a viewing angle enlarging film, a reflective film, an anti-reflection film, an anti-glare film, a luminance improving film, a prism sheet, a microlens array, a conductive film for a touch panel, a film for light guiding and a film for electronic paper; applications to window glass, and interior and exterior of various vehicles other than automobiles such as trains, aircrafts and ships; various packaging containers and packaging materials such as a bottle, a cosmetic container and an accessory case; films for various other applications such as a prize and miscellaneous goods such as an accessory; a surface protective film for a solar cell, a sealing film for a solar cell, a back surface protective film for a solar cell, a base plate film for a solar cell, a green house for agriculture, a protective film for a sound insulating board of a highway, and an outermost surface protective film for a traffic sign.

EXAMPLES

The present invention will be described in detail below with reference to examples, but the present invention is not limited to these examples. The "parts" in the examples means "parts by mass", and "%" means "% by mass".

[Evaluation Method]

Each evaluation in the examples and comparative examples was carried out according to the following methods.

(Evaluation Method for Resin Composition)

(1) Molecular Weight and Molecular Weight Distribution

The mass average molecular weight (Mw), a number average molecular weight (Mn) and the molecular weight distribution (PDI) were measured using gel permeation chromatography (GPC) (manufactured by Tosoh Corporation, brand name: HLC-8220) under the following conditions.

Column: TSK GUARD COLUMN SUPER HZ-L (4.6×35 mm) and two columns of TSK-GEL SUPER HZM-N (6.0× 150 mm) connected in series Eluent: tetrahydrofuran Measurement temperature: 40° C.

Flow rate: 0.6 mL/min

Moreover, Mw and Mn were determined through the use of a calibration curve prepared by using polymethyl methacrylate manufactured by Polymer Laboratories (peak top molecular weight=four tops of 1,590; 10,290; 55,600 and 141,500).

(2) Crystal Melting Enthalpy and Crystallization Temperature

The crystal melting enthalpy of the resin composition was measured in the following manner using a differential scanning calorimeter (manufactured by Hitachi High-Tech Science Corporation, brand name: DSC 6200) according to JIS-K7121, 3. (2).

A sample of the resin composition was heated up to a temperature (approximately 200° C.) higher by approximately 30° C. than that at the end of the melting peak and was melted in an apparatus of DSC, according to JIS-K7121, 3. (2), and was kept at the temperature for 10 minutes.

After that, the sample was cooled to a temperature at least approximately 50° C. lower than the appearing transition peak, at a cooling rate of 10° C./minute. The value of the peak top of the crystallization peak observed in this process was determined to be the crystallization temperature.

Next, the crystal melting enthalpy was calculated from the area of the crystal melting peak observed in the process of temperature rising from 30° C. to 200° C. at 10° C./min. Moreover, in the case where the crystallization peak was observed during the temperature rise, the value obtained by subtracting the area was determined to be the crystal melting enthalpy.

(3) $I_{Hv}$

For the light scattering measurement for determining $I_{Hv}$, the following devices were used: a He—Ne laser (manufactured by JDS Uniphase Corporation, brand name: 1125P-3352, wavelength: 633 nm, output: 10 mW); a glass polarizing filter (manufactured by Edmund Optics Japan Co., Ltd., brand name: high contrast glass polarizing filter, plate thickness: 2 mm, contrast: 10,000); and a CCD camera (manufactured by Toshiba Teli Corporation, brand name: BU 130F, maximum image output number of pixels: 1280× 960). A molded article of a resin composition with a thickness (d) of 200 μm was used as a measurement sample.

The molded article of the resin composition sandwiched between two polarizing plates was irradiated with laser light from a normal direction, the transmitted scattered light was projected onto a screen, and the scattered light was detected by a CCD camera under conditions that the exposure time was 15,000 μs, a gamma value was 1.0 and the sensitivity (gain) was 0. The measurement was carried out in a state in which the directions of the polarization of the two polarizing plates are orthogonal to each other.

The obtained data of 1280×960 on the light amount was compressed into data of 255×191, all of the light amount values were added up, and $A_{Hv}$ was obtained. The similar measurement was carried out also in the case where the molded article was not sandwiched, and $A_{Hv0}$ was obtained. The $I_{Hv}$ was calculated by substituting these $A_{Hv}$ and $A_{Hv0}$ and the thickness d into the above described expression (2).

Moreover, a film having a thickness of 200 μm prepared by a pressing machine was used for the molded article of the resin composition used for measurement of the $I_{Hv}$. The molding conditions for this film will be described later.

(Evaluation Method for Molded Article)

(4) Haze (HZ)

Haze was measured using a haze meter (manufactured by Nippon Denshoku Industries Co., Ltd., brand name: NDH 2000) according to JIS-K7136.

For the test piece, a film having a thickness of 200 μm prepared by a pressing machine in the same manner as in the measurement sample used in the above described (3) was used. Two films for each example were measured, three points for each film were measured, and an average value was determined.

Production Example 1

[Dispersing Agent]

In a reaction vessel having a capacity of 1200 L provided with a stirrer, a cooling tube and a thermometer, 61.6 parts of a 17% aqueous solution of potassium hydroxide; 19.1 parts of methyl methacrylate (manufactured by Mitsubishi Rayon Co., Ltd., brand name: Acryester M); and 19.3 parts of deionized water were placed. Subsequently, the liquid in the reaction vessel was stirred at room temperature, the exothermic peak was checked, and then the liquid was further stirred for 4 hours. After this, the reaction liquid in the reaction vessel was cooled down to room temperature to obtain an aqueous solution of potassium methacrylate.

Subsequently, in a reaction vessel having a capacity of 1050 L provided with a stirrer, a cooling tube and a thermometer, 900 parts of deionized water, 60 parts of sodium 2-sulfoethyl methacrylate (manufactured by Mitsubishi Rayon Co., Ltd., brand name: Acryester SEM-Na), 10 parts of the above described aqueous solution of potassium methacrylate, and 12 parts of the above described methyl methacrylate were placed and stirred, and the temperature was raised to 50° C. while the reaction vessel was purged with nitrogen. In the reaction vessel, 0.08 parts of 2,2'-azobis(2-methylpropionamidine) dihydrochloride (manufactured by Wako Pure Chemical Industries, Ltd., brand name: V-50) was placed as a polymerization initiator and furthermore, the temperature was raised to 60° C. After the temperature was raised, the methyl methacrylate was continuously added dropwise at a speed of 0.24 parts/minute for 75 minutes using a dropping pump. The reaction solution was kept at 60° C. for 6 hours, and was then cooled to room temperature to obtain a dispersing agent having a solid content of 10%, which was a transparent aqueous solution.

Production Example 2

[Macromonomer (1)]

(Synthesis of Cobalt Complex)

In a synthesizing apparatus provided with a stirrer, under a nitrogen atmosphere, 2.00 g (8.03 mmol) of cobalt acetate (II) tetrahydrate (manufactured by Wako Pure Chemical Industries, Ltd., Wako Special grade), 3.86 g (16.1 mmol) of diphenylglyoxime (EP grade, made by Tokyo Chemical Industry Co., Ltd.), and 100 ml of diethyl ether deoxidized beforehand by nitrogen bubbling were placed, and stirred at room temperature for 2 hours.

Subsequently, 20 ml of a boron trifluoride diethyl ether complex (manufactured by Tokyo Chemical Industry Co., Ltd., EP grade) was added and the resulting mixture was further stirred for 6 hours. The obtained reaction liquid was filtered; the solid was washed with diethyl ether and was then dried in the vacuum at 20° C. for 12 hours to obtain 5.02 g (7.93 mmol, yield of 99%) of a brown solid cobalt complex.

(Synthesis of Macromonomer)

In a polymerization apparatus provided with a stirrer, a cooling tube and a thermometer, 145 parts of deionized water, 0.1 parts of sodium sulfate, and 0.26 parts of the dispersing agent (solid content of 10%) produced in Production Example 1 were placed and stirred to form into a uniform aqueous solution. Subsequently, 95 parts of methyl methacrylate (MMA), 5 parts of methyl acrylate (MA) (manufactured by Mitsubishi Chemical Corporation), 0.0016 parts of the above described cobalt complex, and 0.1 parts of Perocta O (manufactured by NOF CORPORATION, 1,1,3,3-tetramethylbutyl peroxy 2-ethylhexanoate, brand name) as a polymerization initiator were added to form into an aqueous dispersion liquid. Subsequently, the polymerization apparatus was sufficiently purged with nitrogen; and the temperature of the aqueous dispersion liquid was raised to 80° C., was kept for 4 hours, then was raised to 95° C., and was held for 1 hour. After that, the reaction liquid was cooled to 40° C. to obtain an aqueous suspension liquid of the macromonomer. This aqueous suspension liquid was filtered through a filter cloth; the filtrate was washed with deionized water, and then was dried at 40° C. for 12 hours to obtain a macromonomer (1). As a result of analysis by GPC, the Mw of the macromonomer (1) was 31,500 and Mn thereof was 14,000. In addition, a value of a solubility parameter (SP value) of the macromonomer (1) (domain (C)) was calculated based on the above described expression (1). The results are shown in Table 1.

Production Example 3

[Macromonomer (2)]

A macromonomer (2) was obtained in the same manner as in Production Example 2, except that the amount of the cobalt complex to be added was changed to 0.0032 parts. As a result of analysis by GPC, the Mw of the macromonomer (2) was 16,000 and Mn thereof was 7,000. The results are shown in Table 1.

TABLE 1

|  |  | Composition (Parts) | | Molecular weight | | SP value |
| --- | --- | --- | --- | --- | --- | --- |
|  |  | MMA | MA | Mw | Mn | domain (C) |
| Production Example 2 | Macromonomer (1) | 95 | 5 | 31500 | 14000 | 19.527 |
| Production Example 3 | Macromonomer (2) | 95 | 5 | 16000 | 7000 | 19.527 |

Production Example 4

[Resin (B1)]

An aqueous solution of a dispersing agent was prepared by mixing 145 parts of deionized water, 0.1 parts of sodium sulfate and 0.26 parts of the dispersing agent produced in Production Example 1.

In a separable flask provided with a cooling tube, 40 parts of the macromonomer (1) synthesized in Production Example 2, 24 parts of methyl methacrylate, 36 parts of n-butyl acrylate (BA) (manufactured by Mitsubishi Chemical Corporation), and 0.1 parts of n-octanethiol (manufactured by Tokyo Chemical Industry Co., Ltd.) were placed, and the mixture was heated to 50° C. while stirring to obtain raw syrup.

After the raw syrup was cooled to 40° C. or lower, 0.3 parts of AMBN (manufactured by Otsuka Chemical Co., Ltd., 2,2'-azobis (2-methylbutyronitrile), brand name) was dissolved in the raw syrup and a syrup was obtained.

Subsequently, the aqueous solution of the above described dispersing agent was added to the obtained syrup, then the number of stirring rotations was increased while the atmosphere in the separable flask was replaced with nitrogen by nitrogen bubbling, and a syrup dispersion liquid was obtained.

The syrup dispersion liquid was heated to 75° C., and the external temperature of the separable flask was kept until a polymerization exothermic peak was observed. When the syrup dispersion liquid reached 75° C., after the polymerization exothermic peak was observed, the syrup dispersion liquid was heated to 85° C. and was kept for 30 minutes to complete the polymerization, and a suspension liquid was obtained.

After the suspension liquid was cooled to 40° C. or lower, the suspension liquid was filtered through a filter cloth; the filtrate was washed with deionized water and was dried at 40° C. for 16 hours to obtain a resin (B1).

The Mw of the resin (B1) was 252,000, the Mn thereof was 40,500, and the molecular weight distribution (PDI) thereof was 6.2. In addition, an SP value of the domain (D) was calculated based on the above described expression (1). The results are shown in Table 2. Moreover, in the resin (B1), the macromonomer (1) is a monomer forming the domain (C), and the MMA and BA are monomers forming the domain (D).

Production Example 5

[Resin (B2)]

A resin (B2) was obtained in the same manner as in Production Example 4, except that 36 parts of methyl methacrylate and 24 parts of n-butyl acrylate were used.

The Mw of the resin (B2) was 143,000, the Mn thereof was 49,000, and the PDI thereof was 2.9. The results are shown in Table 2.

Production Example 6

[Resin (B3)]

A resin (B3) was obtained in the same manner as in Production Example 4, except that the macromonomer (2) was used.

The Mw of the resin (B3) was 259,000, the Mn thereof was 53,000, and the PDI thereof was 4.9. The results are shown in Table 2.

Production Example 7

[Resin (B4)]

A resin (B4) was obtained in the same manner as in Production Example 4, except that 48 parts of methyl methacrylate and 12 parts of n-butyl acrylate were used.

The Mw of the resin (B4) was 65,000, the Mn thereof was 28,500, and the PDI thereof was 2.3. The results are shown in Table 2.

Example 1

[Preparation of Resin Composition]

A resin composition (1) was obtained by dry-blending 40 parts of PVDF (manufactured by Arkema Co., Ltd., brand name: Kynar 720) as the vinylidene fluoride-based resin (A) and 60 parts of the resin (B1) prepared in Production Example 4 as the acrylic-based resin (B); and then melt-kneading the blend at 220° C. by Labo Plastomill (manufactured by Toyo Seiki Co., Ltd.).

[Preparation of Molded Article]

A film-shaped molded article was obtained by placing the resin composition (1) obtained in the above description in a mold made from PTFE; and then pressing (manufactured by Toyo Seiki Co., Ltd., brand name: MINI TEST PRESS-10) the resin composition at 200° C. The cooling was carried out by sandwiching the molded article between metal plates in which cooling water flowed. Moreover, a thickness of the obtained film was 200 μm, and an arithmetic mean roughness (Ra) thereof was 24 nm.

TABLE 2

| | | Composition (Parts) | | | Molecular weight | | | SP value domain |
|---|---|---|---|---|---|---|---|---|
| | | Macromonomer | MMA | BA | Mw | Mn | PDI | (D) |
| Production Example 4 | Resin (B1) | (1) | 40 | 24 | 36 | 252000 | 40500 | 6.2 | 19.775 |
| Production Example 5 | Resin (B2) | (1) | 40 | 36 | 24 | 143000 | 49000 | 2.9 | 19.658 |
| Production Example 6 | Resin (B3) | (2) | 40 | 24 | 36 | 259000 | 53000 | 4.9 | 19.775 |
| Production Example 7 | Resin (B4) | (1) | 40 | 48 | 12 | 65000 | 28500 | 2.3 | 19.533 |

The crystal melting enthalpy, the crystallization temperature, the $A_{Hv}$, the $I_{Hv}$ and the haze (HZ) of the obtained molded article were measured. The evaluation results are shown in Table 3. Moreover, as for the crystallization temperature, "n.d." means that the crystallization peak was not observed.

TABLE 3

| | Resin (A) | | Resin (B) | | SP value (D)-(C) | PTFE | Thermal analysis | | Light scattering | | Optical performance |
|---|---|---|---|---|---|---|---|---|---|---|---|
| | | | | | | | Melting enthalpy | Crystallization temperature | | | |
| | Type | Parts | Type | Parts | — | Parts | [J/g] | [° C.] | $A_{HV}$ | $I_{HV}$ | HZ [%] |
| Example 1 | PVDF | 40 | (B1) | 60 | 0.248 | 0 | 15.0 | 102 | 32104 | 9 | 4.0 |
| Example 2 | PVDF | 50 | (B1) | 50 | 0.248 | 0 | 25.6 | 118 | 33427 | 16 | 4.6 |
| Example 3 | PVDF | 50 | (B2) | 50 | 0.131 | 0 | 22.3 | 112 | 31301 | 5 | 3.2 |
| Example 4 | PVDF | 40 | (B3) | 60 | 0.248 | 0 | 20.2 | 113 | 32524 | 11 | 5.3 |
| Example 5 | PVDF | 40 | (B1) | 60 | 0.248 | 0.1 | 18.1 | 131 | 31196 | 5 | 5.8 |
| Comparative Example 1 | PVDF | 70 | (B1) | 30 | 0.248 | 0 | 32.1 | 139 | 45915 | 78 | 21.4 |
| Comparative Example 2 | PVDF | 100 | — | — | — | 0 | 52.3 | 144 | 127169 | 485 | 54.5 |
| Comparative Example 3 | PVDF | 50 | PMMA | 50 | 0.000 | 0 | 1.8 | n.d. | 30633 | 2 | 1.5 |
| Comparative Example 4 | PVDF | 40 | (B4) | 60 | 0.006 | 0 | 2.7 | n.d. | 30231 | 0 | 1.1 |
| Blank | — | — | — | — | — | — | — | — | 30244 ($=A_{HV0}$) | — | — |

Example 2

A resin composition and a molded article were obtained in the same manner as in Example 1, except that 50 parts of PVDF was used as the vinylidene fluoride-based resin (A) and 50 parts of the resin (B1) was used as the acrylic-based resin (B). The evaluation results are shown in Table 3.

Example 3

A resin composition and a molded article were obtained in the same manner as in Example 1, except that 50 parts of PVDF was used as the vinylidene fluoride-based resin (A) and 50 parts of the resin (B2) prepared as the acrylic-based resin (B) in Production Example 5 was used. The evaluation results are shown in Table 3.

Example 4

A resin composition and a molded article were obtained in the same manner as in Example 1, except that 60 parts of the resin (B3) prepared in Production Example 6 was used as the acrylic-based resin (B). The evaluation results are shown in Table 3.

Example 5

A resin composition and a molded article were obtained in the same manner as in Example 1, except that 0.1 parts of acrylic-modified PTFE (manufactured by Mitsubishi Rayon Co., Ltd., brand name: Metablen A 3800) in terms of PTFE amount was added. The evaluation results are shown in Table 3.

Comparative Example 1

A resin composition and a molded article were obtained in the same manner as in Example 1, except that 70 parts of PVDF was used as the vinylidene fluoride-based resin (A) and 30 parts of the resin (B1) was used as the acrylic-based resin (B). The evaluation results are shown in Table 3.

Comparative Example 2

A resin composition and a molded article were obtained in the same manner as in Example 1, except that 100 parts of PVDF was used as the vinylidene fluoride-based resin (A), and the acrylic-based resin (B) was not used. The evaluation results are shown in Table 3.

Comparative Example 3

A resin composition and a molded article were obtained in the same manner as in Example 1, except that 50 parts of PVDF was used as the vinylidene fluoride-based resin (A) and 50 parts of PMMA (manufactured by Mitsubishi Rayon Co., Ltd., polymethyl methacrylate, brand name: VHK-001) was used as the acrylic-based resin (B). The evaluation results are shown in Table 3.

Comparative Example 4

A resin composition and a molded article were obtained in the same manner as in Example 1, except that 60 parts of the resin (B4) prepared in Production Example 7 was used as the acrylic-based resin (B). The evaluation results are shown in Table 3.

As is understood from the comparison between Examples 1 to 5 and Comparative Examples 1 and 2, when the crystal melting enthalpy is 10 to 45 (J/g) and the $I_{Hv}$ is 60 or less, high crystallinity is kept, the crystals can be refined, and the transparency becomes excellent.

As is understood from the comparison between Examples 1 to 5 and Comparative Examples 3 and 4, when the crystal melting enthalpy is less than 10 (J/g), the crystallinity is insufficient even though the $I_{Hv}$ is 60 or less, and the haze due to the crystallization increases at the time of heating. Specifically, after the molded articles according to Comparative Examples 3 and 4 were subjected to annealing treatment at 100° C. for 3 hours, the hazes were measured again, and as a result, the hazes increased up to 27%.

As illustrated above, the molded article including the vinylidene fluoride-based resin (A) of which the crystal melting enthalpy and the $I_{Hv}$ are values within a predetermined range has the crystal size controlled, accordingly suppresses the light scattering, and has both of high crystallinity and high transparency.

INDUSTRIAL APPLICABILITY

The molded article of the present invention can be suitably used for films for design, films for agriculture, films for vehicle, films for an exterior, films for architectural interior decoration, packaging materials and the like.

The invention claimed is:

1. A resin composition comprising a vinylidene fluoride-based resin (A), having a crystal melting enthalpy of 10 to 45 J/g as measured with a differential scanning calorimeter, and having (2) $I_{Hv}$ of 60 or less as obtained by the following (1) light scattering measurement, wherein (1) the light scattering measurement is a measurement in which a molded article of the resin composition sandwiched between two polarizing plates is irradiated with laser light from a normal direction, the transmitted scattered light is projected onto a screen, and the scattered light is detected with a detector, and (2) the $I_{Hv}$ is a value obtained by converting a difference between a light quantity on the screen when directions of polarization of the two polarizing plates are orthogonal to each other in the (1) light scattering measurement and a light quantity on the screen when the molded article of the resin composition is not sandwiched, into a value per unit thickness (1 μm) of the molded article of the resin composition.

2. The resin composition according to claim 1, wherein the $I_{Hv}$ is 45 or less.

3. The resin composition according to claim 1, further comprising an acrylic-based resin (B).

4. The resin composition according to claim 3, wherein the acrylic-based resin (B) comprises a macromonomer unit.

5. The resin composition according to claim 3, comprising 20 to 60% by mass of the vinylidene fluoride-based resin (A) and 40 to 80% by mass of the acrylic-based resin (B).

6. The resin composition according to claim 3, wherein the acrylic-based resin (B) is a copolymer satisfying the following (3) and (4):

(3) the acrylic-based resin (B) has a domain (C) compatible with the vinylidene fluoride-based resin (A), and a domain (D) different from the domain (C), and (4) a difference in a solubility parameter between the domain (C) and the domain (D) is 0.010 to 0.270.

7. The resin composition according to claim 6, wherein the domain (D) contains 30 to 70% by mass of a monomer unit having the highest mass ratio among monomer units constituting the domain (C).

8. The resin composition according to claim 6, wherein a mass average molecular weight of a polymer or a polymer chain constituting the domain (C) is 5,000 to 45,000.

9. The resin composition according to claim 3, comprising 0.01 to 3.0 parts by mass of polytetrafluoroethylene per 100 parts by mass in total of the vinylidene fluoride-based resin (A) and the acrylic-based resin (B).

10. The resin composition according to claim 3, comprising acrylic-modified polytetrafluoroethylene so that a content of polytetrafluoroethylene is 0.01 to 3.0 parts by mass per 100 parts by mass in total of the vinylidene fluoride-based resin (A) and the acrylic-based resin (B).

11. A molded article obtained by molding the resin composition according to claim 1.

12. A film obtained by molding the resin composition according to claim 1.

13. The film according to claim 12, having a thickness of 350 μm or less.

14. The film according to claim 12, having an arithmetic mean roughness of a surface of 50 nm or less.

* * * * *